US012594363B2

(12) United States Patent
Moyer et al.

(10) Patent No.: US 12,594,363 B2
(45) Date of Patent: Apr. 7, 2026

(54) ENHANCED BIOLOGIC GRAFTS WITH PACKAGING APPARATUSES, AND METHODS OF USE

(71) Applicant: XoBiologix, L.L.C., Austin, TX (US)

(72) Inventors: Mary Pat Moyer, San Antonio, TX (US); David Janice, Austin, TX (US)

( * ) Notice: Subject to any disclaimer, the term of this patent is extended or adjusted under 35 U.S.C. 154(b) by 868 days.

(21) Appl. No.: 17/684,135

(22) Filed: Mar. 1, 2022

(65) Prior Publication Data

US 2023/0277727 A1 Sep. 7, 2023

(51) Int. Cl.
*A61L 27/36* (2006.01)

(52) U.S. Cl.
CPC ....... *A61L 27/3691* (2013.01); *A61L 27/3604* (2013.01)

(58) Field of Classification Search
CPC ................................................. A61L 27/3604
See application file for complete search history.

(56) References Cited

U.S. PATENT DOCUMENTS

| | | | |
|---|---|---|---|
| 2016/0000968 A1* | 1/2016 | Koob | A61L 27/3604 623/23.72 |
| 2016/0129154 A1* | 5/2016 | Hopkinson | A61L 27/3687 424/582 |
| 2021/0169647 A1* | 6/2021 | Matheny | A61L 27/225 |
| 2022/0047774 A1* | 2/2022 | Imming | A61L 27/3604 |
| 2022/0133955 A1* | 5/2022 | McQueen | A61F 2/0063 623/23.74 |
| 2022/0280693 A1* | 9/2022 | Nichols | A61L 27/3687 |
| 2023/0347015 A1* | 11/2023 | Koob | A61K 35/50 |
| 2023/0390457 A1* | 12/2023 | Tofe | A61L 27/3604 |
| 2023/0398260 A1* | 12/2023 | Tseng | A61K 35/50 |
| 2024/0050482 A1* | 2/2024 | Tom | A61P 17/02 |

* cited by examiner

*Primary Examiner* — Philip R Wiest
*Assistant Examiner* — Meagan Ngo
(74) *Attorney, Agent, or Firm* — Lexigent LLC

(57) ABSTRACT

Enhanced biologic grafts with packaging apparatuses, and methods of use are disclosed herein. An example apparatus can include a vessel comprising a port that is configured to allow a fluid to be introduced into the vessel and a membrane placed within the vessel. The membrane is lyophilized prior to placement into the vessel. The membrane is sealed within the vessel and the port can be used to introduce a fluid into the vessel to reconstitute the membrane while sealed inside the vessel.

19 Claims, 5 Drawing Sheets

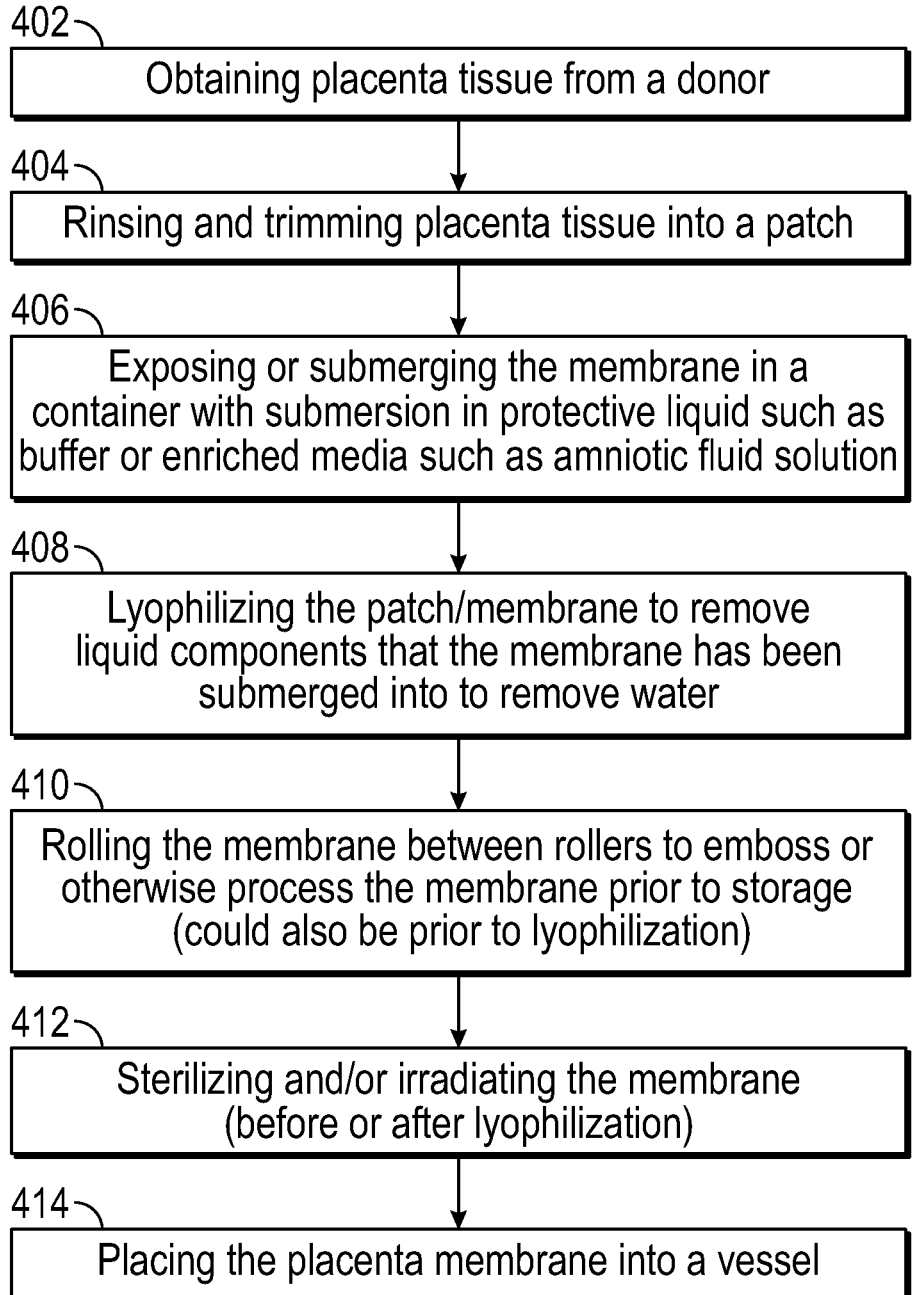

402 — Obtaining placenta tissue from a donor

404 — Rinsing and trimming placenta tissue into a patch

406 — Exposing or submerging the membrane in a container with submersion in protective liquid such as buffer or enriched media such as amniotic fluid solution 408 — Lyophilizing the patch/membrane to remove liquid components that the membrane has been submerged into to remove water 410 — Rolling the membrane between rollers to emboss or otherwise process the membrane prior to storage (could also be prior to lyophilization)

412 — Sterilizing and/or irradiating the membrane (before or after lyophilization)

414 — Placing the placenta membrane into a vessel

FIG. 4

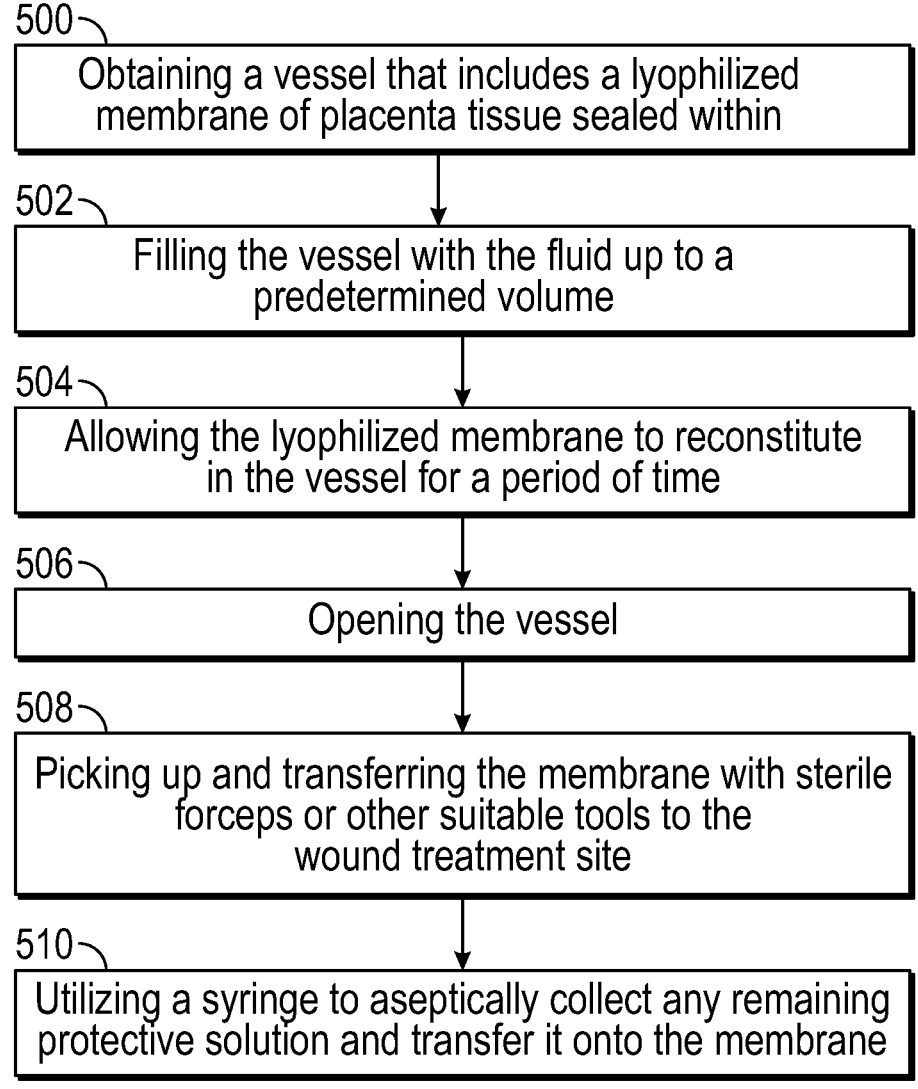

500
Obtaining a vessel that includes a lyophilized membrane of placenta tissue sealed within 502
Filling the vessel with the fluid up to a predetermined volume 504
Allowing the lyophilized membrane to reconstitute in the vessel for a period of time 506
Opening the vessel 508
Picking up and transferring the membrane with sterile forceps or other suitable tools to the wound treatment site 510
Utilizing a syringe to aseptically collect any remaining protective solution and transfer it onto the membrane

FIG. 5

ENHANCED BIOLOGIC GRAFTS WITH PACKAGING APPARATUSES, AND METHODS OF USE

CROSS-REFERENCE TO RELATED APPLICATION(S)

N/A.

TECHNICAL FIELD

The present disclosure pertains to biologic products, and more particularly, but not by way of limitation, to placenta-derived membrane tissue grafts that can be packaged in such a way that the membrane grafts can be easily reconstituted while in their package and prior to application to a wound.

SUMMARY

According to some embodiments, the present disclosure is directed to an apparatus comprising a vessel containing a port that is configured to allow a fluid to be introduced into the vessel; and a tissue membrane in a minimal volume of protective solution is sealed within the vessel, wherein the tissue membrane is lyophilized within the vessel, the port is configured to allow a fluid to be introduced into the vessel to easily reconstitute the membrane while the membrane is sealed inside the vessel. In one embodiment, the membrane is a placenta membrane that comprises at least one of a chorion layer and/or an amnion layer, and by example was not previously integral, or attached and detached as in derived from umbilical cord amnion In some embodiments, the port is adapted to receive the fluid to reconstitute the placenta membrane, or membranes prior to use. The port may be adapted to allow an enriched fluid created by reconstitution of the placenta membrane to be extracted from the vessel. In some embodiments, the vessel comprises a jar with a lid, and the port is a septum associated with the lid. In another embodiment, the vessel comprises a sterile bag.

In various embodiments, a rolling mechanism can be is used to roll or knead the membrane while in the vessel and after a fluid has been introduced into the vessel to reconstitute the lyophilized membrane, as well as to assure a controlled rehydration. The rolling mechanism can be used to knead and enhance rehydration. In one embodiment, the rolling mechanism comprises a first roller and a second roller. The first roller and the second roller can be placed in vertical alignment with one another. Also, the first roller and the second roller can be spaced apart from one another at a slight distance D. The vessel and the membrane are laterally translated in a space in such a way that the first roller and the second roller exert a rolling or kneading force onto the membrane. In some instances, the first roller and the second roller are coupled together using a resilient coupler. In some instances, at least one of the first roller and the second roller are embossed to transfer a pattern onto the membrane.

According to some embodiments, the present disclosure can be directed to a method comprising creating a placenta membrane by: obtaining amnion tissue from a donor; obtaining chorion tissue from a donor, obtaining umbilical cord amnion and subepithelial tissues, and then sizing each tissue by cutting it into patches; and lyophilizing the patches; and placing the placenta membrane tissue into a vessel, the vessel having a port that is configured to receive a fluid used to reconstitute the placenta membrane tissue prior to use.

The method can include an optional step of sterilizing the placenta membrane tissues and/or irradiating the placenta membrane tissues. The method can include a step of reconstituting the placenta membrane by: filling the vessel with the fluid up to a predetermined volume; opening the vessel and removing the membrane tissue; and applying the placenta membrane tissue that has been reconstituted to a wound of a patient.

The method can also include a step of extracting from the vessel an overage of enriched fluid created and remaining following reconstitution of the placenta membrane. The enriched fluid can be applied to the wound before and/or after placement of the placenta membrane on the wound.

The method can also include kneading or embossing the placenta membrane. In one or more embodiments, the method includes rolling the placenta membrane between rollers when the placenta membrane is in the vessel and a reconstituting fluid has been placed into the vessel. In some embodiments, this includes embossing the placenta membrane using rollers that may have pattern embossments.

According to some embodiments, a method can include obtaining a vessel that comprises a port, the vessel sealing a lyophilized membrane of placenta tissue within; rehydrating the lyophilized membrane to create a rehydrated membrane by introducing a fluid into the port; extracting the fluid that might have been enriched by the rehydration of the lyophilized membrane; obtaining the rehydrated membrane; applying the rehydrated membrane to a wound of a patient; and applying any remaining fluid that was not absorbed and possibly has been enriched to the rehydrated membrane.

In other embodiments, placental membrane might be coupled with collagen additives, synthetic polymer sheets, or extracted interstitial fluids from other tissues. In example, muscle distillate might be collected, placed onto various forms of biomaterials including placental membranes, collagen membranes, synthetic membranes and then further lyophilized prior to placement with the vessel. This process guides specificity of content to tissue type. In this example, muscle distillate in context of anti-inflammatory factors might be used to guide muscle tendon repair. Distillates in this iteration, could represent passive elution, fluid extraction, continuous cyclic pressure variation, with the intent to capture micromolecular, macromolecular, and nanomolecular solute that define tissue communication.

In still other embodiments, non-whole cell constituents such as conditioned media, secretome-rich culture supernatant, exosomes, or naked DNA plasmid or regulatory RNA might be introduced as part of the post-lyophilization process to imbue the reconstitution with factors separate than and in addition to the original constituent factors of placental tissue, collagen matrices, or synthetic scaffolds that might be adapted and adopted to this use.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

FIG. 4 is a flowchart of an example method of the present disclosure.

FIG. 5 is a flowchart of another example method of the present disclosure.

DETAILED DESCRIPTION

Overview

Figure 1:
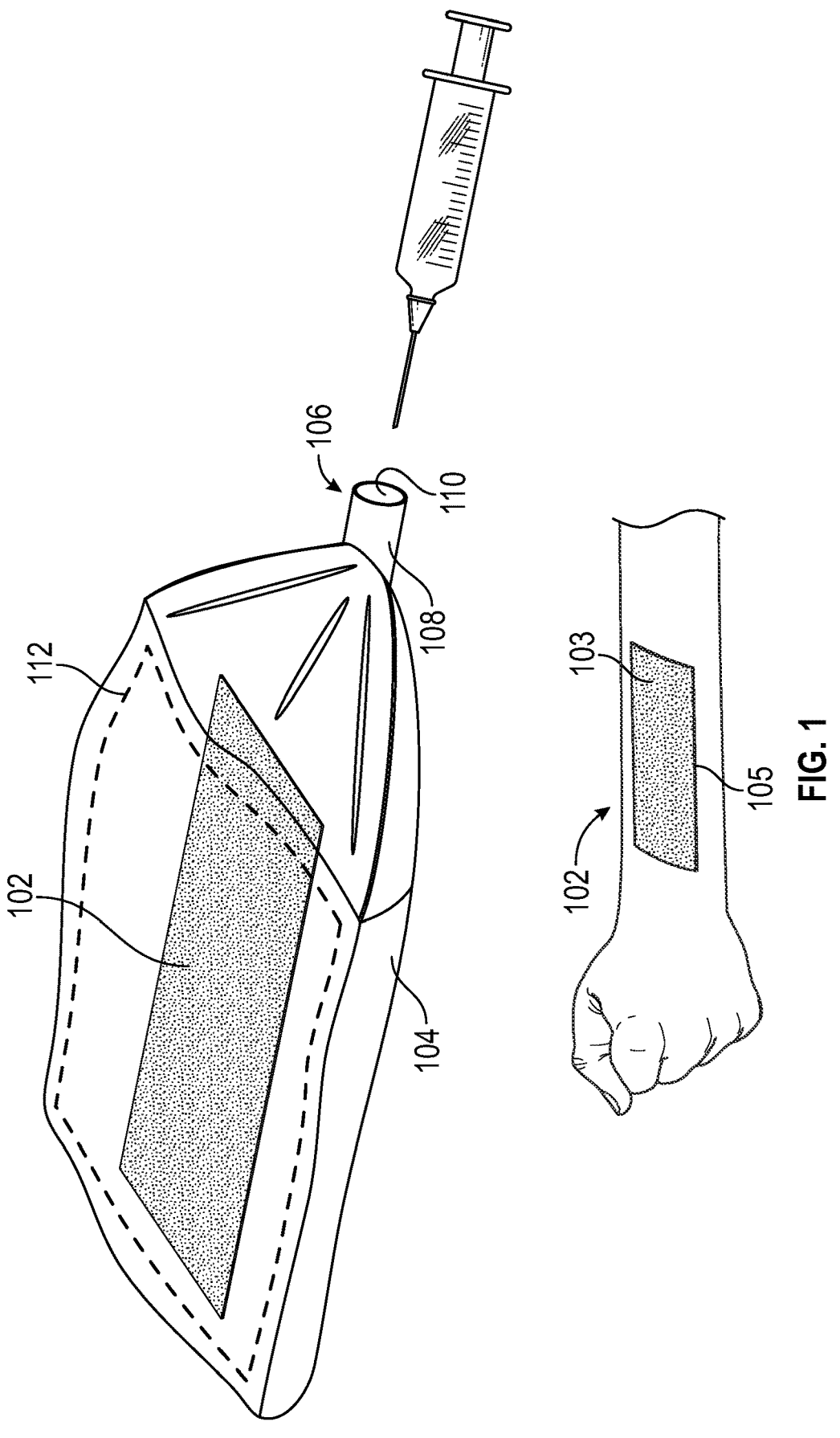
FIG. 1 is a perspective view of an example apparatus of the present disclosure.

The present disclosure is directed to biologic tissue grafts are apparatuses for packaging the same. In general, the biologic grafts of interest are membranes that are derived from placental tissues. In some embodiments, the placental membrane tissue can be derived from a separated amnion sheet or a separated chorion sheet or be comprised of both an amniotic layer and a chorion layer. In one embodiment the membrane tissue is kept wetted in a small volume of protective solution prior to lyophilization. In another consideration, a placental membrane from umbilical cord that is defined by amnion and subepithelial tissue including Wharton's Jelly would be processed and packaged in the apparatus.

In some embodiments, membranes can be lyophilized and terminally sterilized by irradiation so that they do not contain live, replicative cells. Once the membrane has been lyophilized it can be sealed in a vessel. The vessel can include a port that is configured to allow a fluid to be introduced into the vessel to reconstitute the membrane while the membrane is sealed inside the vessel. In one embodiment, the vessel is a sealed bag. In another embodiment, the vessel is a jar with a septum.

As noted above, the membrane can be reconstituted with a fluid, such as saline, buffered salt solution or an equivalent that would be known to one of ordinary skill in the art. A reconstituted membrane can be used as a single-use regenerative repair tissue product for covering and management of wounds. Example wounds or conditions include, but are not limited to, partial or full-thickness wounds, ulcers, that are chronic or non-healing; and may include but not limited to diabetic, pressure, venous or vascular types. Other wounds include surgical or treatment wounds that include, but not limited to donor sites for grafts, spinal surgery coverings, podiatric use, skin wounds, post-laser surgery, non-closing wounds or draining wounds, and radiation damage—just to name a few. Additional example wounds include trauma wounds that include, but are not limited to, lacerations, punctures, second-degree burns, skin tears, or abrasions, where the introduced tissue barrier would provide protection and hydration to facilitate repair and buffer the distribution of inflammatory cytokines.

Example Embodiments

Embodiments disclosed herein involve the creation and packaging of placental tissue-derived amniotic and/or chorionic membrane products for use in wound treatment. Prior to discussing the packaging and use of these membranes, example methods for producing a membrane are disclosed herein.

In some embodiments, a membrane product can be manufactured from placenta tissue. A membrane can be from a chorion layer and/or an amnion layer. In various embodiments, the membrane product may be processed in a protective solution and can include a carrier substrate that is manufactured from a suitable biologic matrix. The chorion layer can be laminated to one side/surface of the matrix and the amnion layer can be laminated to the opposing side/surface. In some instances, the chorion layer and the amnion layer are in direct contact with one another. In other embodiments, the membrane can include only a chorion layer. A chorion will be understood to include an outermost membrane surrounding an embryo. The chorion contributes to the formation of the placenta.

In yet other embodiments, the membrane can include only an amnion layer. The amnion is a membrane that closely covers the human and various other embryos when first formed. It fills with amniotic fluid, which causes the amnion to expand and become the amniotic fluid filled amniotic sac that provides a protective environment for the embryo through fetal development to birth.

In some embodiments, the membrane can include a polymer substrate that is particularly adapted for use with wound healing and the like. The polymer substrate can be chosen from any desired, medically suitable substrate that would be known to one of ordinary skill in the art. Some embodiments may include a layer of a polymeric material in combination with other layers such as chorion and amnion tissue. The arrangement and placement of layers can vary according to design requirements and use cases. An example substrate could include, but is not limited to, DACRON.

According to some embodiments, the membrane can be submerged in amniotic fluid solution prior to lyophilization. To be sure, the amniotic fluid and/or membrane comprise enriching components such as extracellular matrix (ECM), salts, sugars, proteins, glycoproteins, lipids, collagen, chemokines, cytokines, growth factors, hyaluronan, various regulatory molecules, ribonucleic acids RNAs, amino acids, lipids, lipoproteins, and peptides, and other cell and tissue building blocks—just to name a few.

It will be understood that in some embodiments, the membrane and amniotic fluid solution can be introduced into the vessel and lyophilized therein. In other embodiments, a lyophilized membrane tissue can be placed into the vessel. That is, the membrane and an enriching fluid can be lyophilized in a first process and added to the vessel after lyophilization.

Cryo-lyophilization of the membrane in the submersed fluid yields a barrier membrane with placental liquid components removed. That is, lyophilization freeze-dries liquid components while leaving the enriching components associated with the membrane. The placental tissue membranes can be cut and rinsed prior to, or after lyophilization. The tissue can be cut and rinsed during harvesting as well. In some embodiments, the membrane can be sterilized and/or irradiated to ensure that no living cells are present.

Once the membrane has been prepared, the membrane can be placed into a vessel. FIG. 1 illustrates an example vessel, which is a sterile bag configured to receive and retain a membrane 102 of the present disclosure with an amnion layer 103 and a chorion layer 105. To be sure, the relative orientations of the layers can be reversed. The vessel is in the form of a bag 104. The bag 104 can be manufactured from any suitable material that would be known to one of ordinary skill in the art. The bag 104 can be sterilized prior to placement of the membrane 102 therein. The bag 104 can include a port 106 that is configured to allow a fluid to be introduced into the vessel to reconstitute the membrane while the membrane is sealed inside the vessel. This can be heat-sealed or otherwise treated to allow closure as a closed system.

As noted throughout, the fluid used to reconstitute the membrane 102 can include saline, although other fluids can be used. Moreover, in addition to a reconstituting fluid, a user can also introduce an augmenting or enhancing product such as platelet-rich plasma, platelet poor plasma, amniotic fluid and/or bone marrow aspirate—just to name a few.

In one embodiment, the port 106 includes a tubular body 108 with a port membrane 110. The port membrane 110 can include any material that allows a needle of a syringe to be inserted into the port 106 to introduce fluid into the bag 104. One example membrane can include a septum. The bag 104 can include a peelable cover 112. A user can rapidly access the membrane by removing the peelable cover 112. It will be understood that the bag 104 can be manufactured without the port 106. The membrane can be reconstituted by removing the peelable cover 112 or otherwise opening the bag. A user can fill the bag with a predetermined volume of fluid to reconstitute the membrane. Prior to opening the bag 104 and after the fluid has been placed into the bag, the user may allow the membrane 102 to reconstitute for a period of time. During this reconstitution process, enriching components may be released or slough off of the membrane 102 and reenter the liquid. This enriched fluid (e.g., solution) can be used in wound treatment as well. Thus, the port 106 is adapted to allow submerging fluid to be added to the original membrane or to become an enriched fluid upon reconstitution of the placenta membrane and to be extracted from the vessel.

In some embodiments, the fluid can be introduced into the bag during a procedure. That is, the lyophilized tissue membrane may not be reconstituted until immediately before application to a wound. In other embodiments, the fluid can be introduced into the bag during manufacturing (e.g., pre-moistening of the membrane).

Figure 2A:
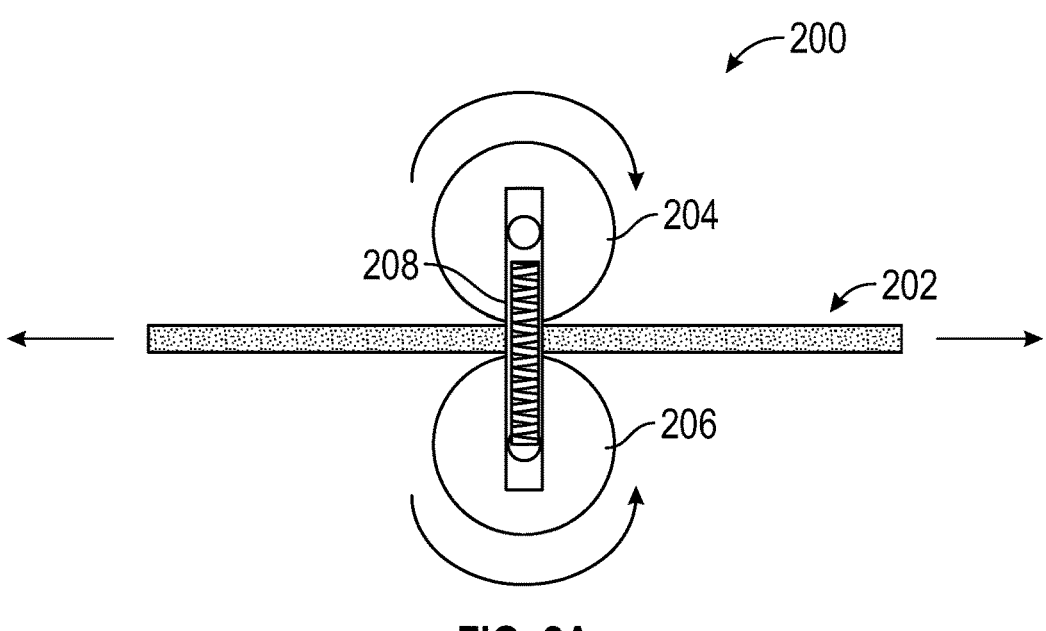
FIG. 2A is a perspective view of an example rolling mechanism used to process a membrane.

FIG. 2A illustrates an example rolling mechanism or apparatus 200 that can be used to process a packaged membrane 202 prior to application to a wound. A packaged membrane can include a lyophilized membrane that is sealed in a bag or other similar malleable packaging (as opposed to a rigid container such as a glass jar). The apparatus 200 can include a first roller 204, a second roller 206, and a resilient coupler 208. In some embodiments, the first roller 204 and the second roller 206 are placed in vertical alignment with one another. When at rest, the first roller 204 and the second roller 206 may be drawn into contact with one another using the resilient coupler 208. When the packaged membrane 202 is inserted between the first roller 204 and the second roller 206, the tension that is applied by the resilient coupler 208 may cause the first roller 204 and the second roller 206 to exert force on the packaged membrane 202 as the packaged membrane 202 is moved forwards and backward. Stated otherwise, the vessel and the membrane are laterally translated between the rollers in such a way that the first roller and the second roller exert a rolling or kneading force onto the membrane due to the action of the resilient coupler 208.

In one embodiment, the resilient coupler 208 could include a spring that is tensioned to draw the first roller 204 and the second roller 206 into contact with one another when the apparatus is at rest. The spring can be coupled to the first roller 204 at one end and to the second roller 206 at an opposing end of the springs. When the membrane is rolled between the first roller 204 and the second roller 206, the spring continues to exert forces on the first roller 204 and the second roller 206, which are then imparted to the membrane by the first roller 204 and the second roller 206.

In some embodiments, the rolling mechanism 200 can be used to roll or knead the membrane while in the vessel and after a fluid has been introduced into the vessel to reconstitute the membrane. To be sure, the rolling mechanism 200 can also be used to preprocess a membrane prior to lyophilizing or after lyophilizing, and prior to placing the membrane in the vessel.

Figure 2B:
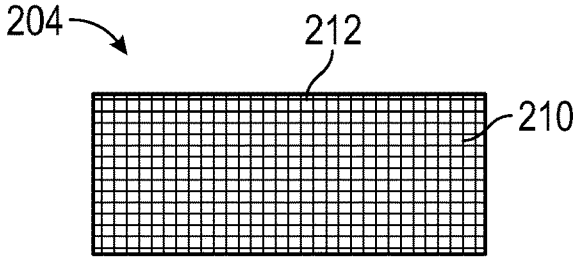
FIG. 2B illustrates an example roller that includes a raised pattern embossing surface.
Figure 2C:
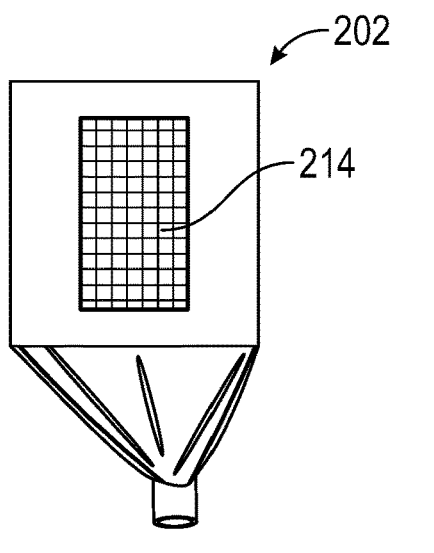
FIG. 2C illustrates an example membrane in a vessel that has been embossed by a roller.

In some embodiments, as illustrated in FIG. 2B, either the first or second roller can be embossed. For example, an outer surface 210 of the first roller 204 can comprise embossing 212 or another pattern. The embossing 212 transfers a pattern 214 onto the packaged membrane 202 as illustrated in FIG. 2C. Again, as noted above, the apparatus can be used to emboss a membrane prior to lyophilization as well.

Figure 3:
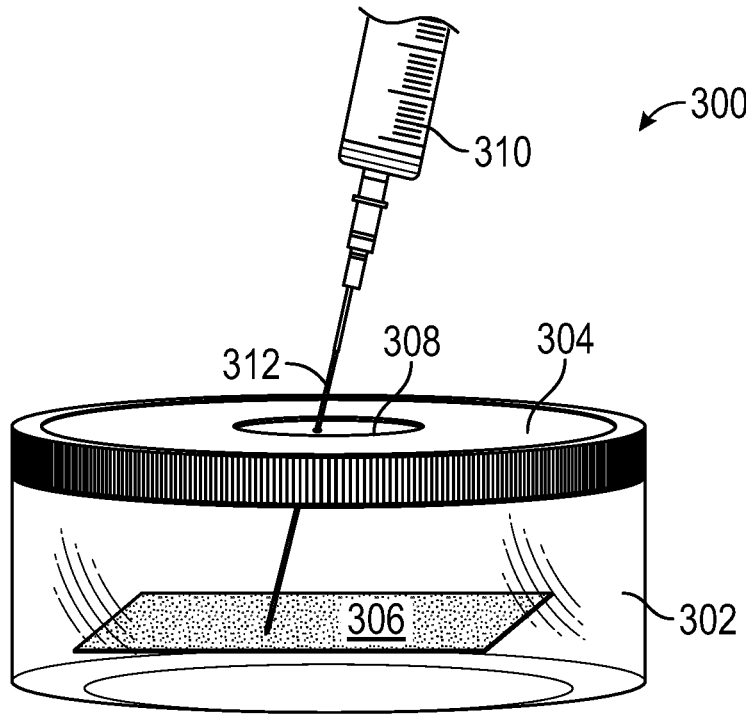
FIG. 3 illustrates another example vessel for storing a lyophilized membrane, the vessel being a jar with a septum lid.

FIG. 3 is a perspective view of another example vessel in the form of a jar 300. The jar 300 can include a body 302 and a lid 304. While the jar 300 is illustrated as having a substantially cylindrical shape, other shapes can also be used. A lyophilized membrane 306 can be placed into the body 302 and the lid 304 is joined to the body 302. In one example, the lid 304 can be threaded onto the body 302. That is, each of the lid and body has complementary threads that can interface to allow the lid to be secured to the body 302. While a threaded coupling has been disclosed, other means for coupling can be used such as a compression fitting, or another similar means that would be known to one of ordinary skill in the art with the present disclosure before them.

In some embodiments, the lid 304 can include a septum 308. As noted above, the septum 308 can include any membrane that maintains a seal within the jar 300 but allows for the introduction of fluid into the jar. For example, a user can introduce saline into the jar 300 with a syringe 310. A needle 312 of the syringe 310 penetrates the septum 308. The syringe is used to deliver a fluid such as saline into the jar. As noted above, the fluid rehydrates the membrane 306. A user can remove the lid 304 after reconstitution of the membrane 306 and use the same to treat a wound. In some instances, the user can extract enriched fluid from the jar prior to opening the lid 304. This enriched fluid, as noted above, is created when material that was lyophilized with the tissue to create the membrane mixes with the fluid used to reconstitute the membrane 306. The enriched fluid can be used to pretreat the wound to prepare the wound to receive the membrane. The enriched fluid can also be used to wash the membrane once it has been applied to the wound. In some embodiments, the user can extract the enriched fluid, not through the septum 308, but after the lid 304 is removed and the tissue is prepared for use.

It will be understood that the amount of fluid introduced into the jar can vary according to the specific configuration of the lyophilized membrane. For example, more fluid may be required to reconstitute a membrane that has a cross-section or other dimension that is larger relative to a smaller membrane of equivalent chorion/amnion composition.

In some embodiments, it may be advantageous to employ a scoop, paddle, tongs, forceps or other implement to assist transfer and removal of the reconstituted membrane from the jar. Using a sterilized transfer implement may reduce a likelihood that the reconstituted membrane may be deleteriously contaminated.

To be sure, in some instances, a vessel of the present disclosure (bearing a lyophilized membrane) can be packaged along with a syringe and/or implement to remove the lyophilized membrane from the vessel. These items can be assembled as a kit that can be sterilized and delivered to a user in a single package.

FIG. 4 is a flowchart of an example method creating a lyophilized membrane (e.g., placental amnion and/or chorion-derived membrane). The method can include a step 402 of obtaining placenta tissue from a donor. This can also include steps such as obtaining amnion and/or chorion from a donor, obtaining umbilical cord amnion and subepithelial tissues, and then sizing the tissue by cutting. The amnion tissue in this example is a combination of a plurality of tissue substrate options obtained from a donor. Thus, any reference disclosed herein related to amnion tissue can include not only purely amnion tissue, but two or more types of tissues having different properties relative to one another. Also, while some embodiments disclose creating a single lyophilized membrane, the same processes can be used to create a plurality of lyophilized membranes.

The method can include a step 404 of rinsing and trimming placenta tissue into a patch. In some embodiments, the patch includes both a chorion layer and an amnionic layer. In some embodiments, the creation of the patch can include a single layer patch, or laminating the layers of the membrane together from separate elements.

The method can include a step 406 of exposing or submerging the membrane in a reservoir of enrichment fluid. As with the amnion and/or chorion membrane, the enrichment fluid can include various types of components that are used to enrich the underlying placental tissue such as platelet-rich plasma, platelet poor plasma, amniotic fluid solution and/or bone marrow aspirate. In other embodiments, additional substances can be used such as a medicament or the like that may assist in wound healing and prevent infection and/or rejection of the graft membrane. Generally, an enriched membrane is a placental tissue (as a single tissue or combination of tissues) that has been in contact with an enriched fluid, for submersion or reconstitution, and having one or more components as elucidated above.

In one embodiment, the method can include a step 408 of lyophilizing the patch/membrane to remove liquid components that the membrane has been submerged into. This step can remove water while other components remain such as extracellular matrix (ECM), salts, sugars, proteins, glycoproteins, lipids, collagen, chemokines, cytokines, growth factors, hyaluronan, various regulatory molecules, ribonucleic acids RNAs, amino acids, lipids, lipoproteins, and peptides, and other cell and tissue building blocks. The resultant product is a highly enriched membrane tissue that can be stored in a vessel.

In some embodiments, the method can include a step 410 (which could occur before step 408 as well) of rolling the membrane between rollers to emboss or otherwise process the membrane prior to storage. As noted above, the membrane can be rolled between two vertically aligned rollers. When one or more of these rollers is provided with a raised embossed pattern, the membrane is embossed with the pattern.

The method can include a step 412 of sterilizing and/or irradiating the membrane. Once sterilized, the method can include a step 414 of placing the placenta membrane into a vessel. In some instances, the vessel has a port that is configured to receive a fluid used to reconstitute the placenta membrane prior to use.

FIG. 5 is a flowchart of a related method for reconstituting and using a stored lyophilized membrane. The method can include a step 500 of obtaining a obtaining a vessel that includes a lyophilized membrane of placenta tissue sealed within. As noted, the vessel can include a port.

The method can include a step 502 of filling the vessel with the fluid up to a predetermined volume. As noted, the filling of the vessel can include injecting fluid, such as saline, into the vessel through the port associated with the vessel. The method can include a step 504 of allowing the lyophilized membrane to reconstitute in the vessel for a period of time. In some instances, the user can gently swirl periodically over a 10-to-15-minute period to assure the membrane and its lyophilization components are homogeneously rehydrated by the saline.

After rehydration/reconstitution, the method can include a step 506 of the user opening the vessel (either by peeling a bag open when the vessel is a bag or removing the lid when the vessel is a jar). The method can include a step 508 of the user picking up and transferring the membrane with sterile forceps or other suitable tools to the wound treatment site. Optionally, the method can include a step 510 of the user utilizing a syringe to aseptically collect any remaining protective solution and transfer it onto the membrane. Stated otherwise, the user extracts from the vessel an enriched fluid created upon reconstitution of the lyophilized membrane, and control of the eluant is assured.

As noted above, the user can apply a portion of the solution to the wound before and/or after placement of the membrane. In sum, to enhance handling, fluid can be removed from the port of the vessel (such as a septum), and when placed as a therapeutic barrier, the solution can be reapplied to assure full measure of therapeutic content is delivered.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three-dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass-ceramic, an organic solid, such as and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scented coating and/or any combinations thereof.

The corresponding structures, materials, acts, and equivalents of all means or steps plus function elements in the claims below are intended to include any structure, material, or act for performing the function in combination with other claimed elements as specifically claimed. The description of the present technology has been presented for purposes of illustration and description but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

In this description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

That which is claimed is:

1. A method comprising:
creating a placenta membrane by:
obtaining amnion tissue from a donor;
cutting the amnion tissue into a patch;
lyophilizing the patch; placing the placenta membrane into a vessel, the vessel having a port that is configured to receive a fluid used to reconstitute the placenta membrane prior to use; and
rolling the placenta membrane between rollers when the placenta membrane is in the vessel and a reconstituting fluid has been placed into the vessel, the placenta membrane being embossed by the rollers.

2. The method according to claim 1, further comprising sterilizing the placenta membrane.

3. The method according to claim 2, further comprising irradiating the placenta membrane.

4. The method according to claim 3, further comprising reconstituting the placenta membrane by:
filling the vessel with the fluid up to a predetermined volume;
opening the vessel; and
applying the placenta membrane that has been reconstituted to a wound of a patient.

5. The method according to claim 4, further comprising extracting from the vessel an enriched fluid created by reconstitution of the placenta membrane.

6. The method according to claim 5, further comprising applying the enriched fluid to the wound before and/or after placement of the placenta membrane on the wound.

7. The method according to claim 4, further comprising filling the vessel with saline and allowing the placenta membrane to rehydrate for a period of at least 10 minutes before opening the vessel.

8. The method according to claim 4, further comprising removing the reconstituted placenta membrane from the vessel using a sterile implement selected from the group consisting of forceps, tongs, and a scoop before applying it to the wound.

9. The method according to claim 1, further comprising enriching the placenta membrane with any one or more of plasma rich platelets, platelet poor plasma, and/or bone marrow aspirate.

10. The method according to claim 9, further comprising submerging the placenta membrane in a solution containing at least one of platelet-rich plasma or bone marrow aspirate and laminating the placenta membrane to a collagen matrix before lyophilizing the patch.

11. The method according to claim 1, further comprising obtaining chorion tissue from the donor, cutting the chorion tissue into a patch, and lyophilizing the chorion patch with the amnion patch to form the placenta membrane comprising both the amnion patch and the chorion patch.

12. The method according to claim 11, further comprising enriching the placenta membrane by submerging the amnion patch and the chorion patch in a solution containing platelet-rich plasma before lyophilizing.

13. The method according to claim 1, further comprising rinsing the amnion tissue and submerging the amnion patch in an enrichment fluid comprising amniotic fluid solution before lyophilizing the patch.

14. The method according to claim 1, further comprising selecting a sterile bag as the vessel, the sterile bag having a septum port configured to allow injection of the fluid for reconstitution.

15. The method according to claim 1, further comprising selecting a jar with a lid as the vessel, the lid including a septum port configured to allow injection of the fluid for reconstitution.

16. The method according to claim 1, further comprising coupling the placenta membrane with a substrate selected from the group consisting of a collagen matrix and a synthetic polymer sheet before placing the placenta membrane into the vessel.

17. The method according to claim 1, further comprising introducing non-whole cell constituents selected from conditioned media, exosomes, and/or regulatory RNA into the vessel after placing the placenta membrane and before reconstituting the placenta membrane.

18. The method according to claim 1, further comprising obtaining umbilical cord amnion tissue from the donor, cutting the umbilical cord amnion tissue into a patch, and lyophilizing the umbilical cord amnion patch with the amnion patch to form the placenta membrane.

19. The method according to claim 11, further comprising embossing a therapeutic design onto the placenta membrane by using rollers with a raised pattern during rolling.

* * * * *